United States Patent [19]

Frevel et al.

[11] 4,101,451

[45] Jul. 18, 1978

[54] ENHANCEMENT OF PROMOTED COPPER CATALYST

[75] Inventors: Ludo K. Frevel, Midland; Leonard J. Kressley, Saginaw, both of Mich.

[73] Assignee: The Dow Chemical Company, Midland, Mich.

[21] Appl. No.: 760,775

[22] Filed: Jan. 19, 1977

[51] Int. Cl.² .................. B01J 21/04; B01J 23/72; B01J 23/56; B01J 23/74

[52] U.S. Cl. .................. 252/465; 252/463; 252/466 J; 252/466 PT

[58] Field of Search .................. 252/411 S, 463, 465, 252/466 J, 466 PT

[56] References Cited

U.S. PATENT DOCUMENTS 3,327,013  6/1967  Frevel et al. .................. 252/412 X
3,912,789  10/1975  Frevel et al. .................. 260/677 H

*Primary Examiner*—W. J. Shine

[57] ABSTRACT

The activity and resistance to sulfur poisoning of a catalyst consisting essentially of copper and one or more activator metals supported on high surface area gamma-alumina and suitable for selectively hydrogenating alpha-acetylenes in a hydrocarbon stream is enhanced by impregnating the catalyst with aqueous alkali metal hydroxide and heating the impregnated catalyst at about 350° C–650° C. This treatment is effective to increase catalytic activity both in freshly prepared catalyst and in used catalyst poisoned by sulfur which has been regenerated by treatment with aqueous alkali metal hydroxide, heating to an elevated temperature, and leaching with water.

6 Claims, No Drawings

ENHANCEMENT OF PROMOTED COPPER CATALYST

BACKGROUND OF THE INVENTION

This invention relates to a process for enhancing the activity of a promoted copper catalyst useful for selectively hydrogenating alpha-acetylenes in the presence of olefins in a liquid hydrocarbon stream.

Product streams of normally liquid or liquefiable olefins and diolefins such as propylene, butenes, pentenes, butadiene, and isoprene in particular are usually contaminated with small amounts of acetylenic impurities which are undesirable and often have to be removed at least to the level of a few parts per million in order for the stream to meet process requirements, for example, in polymerization processes or to avoid formation of explosive metal acetylides in equipment. These acetylenic impurities are essentially the alpha-acetylenes corresponding to the olefins and diolefins present as listed above.

It is known that acetylenic impurities can be selectively hydrogenated and thereby removed from a gas stream by passing a mixture of the gas with hydrogen over a copper catalyst of moderate activity. Such a method is described in our U.S. Pat. Nos. 3,076,858 and 3,327,013. More recently, a highly activated copper catalyst has been found to be very effective for removing acetylenic contaminants from a hydrocarbon stream by catalyzing the selective reduction of alpha-acetylenes with hydrogen dissolved in the liquid hydrocarbon stream. This process is described in our U.S. Pat. No. 3,912,789.

Previously known methods for regenerating this catalyst after its activity has declined substantially upon prolonged use have been based on repeated reduction by hydrogen. Although such regeneration is effective in many cases, when the loss of catalyst activity is caused by the cumulative effect of sulfur compounds present in the stream being treated, hydrogen reduction is relatively ineffective. Sulfur compounds commonly encountered include $H_2S$, lower alkyl mercaptans, organic sulfides and disulfides, COS, $SO_2$, and $SO_3$. Furthermore, when the stream is contaminated by more than the merest traces of sulfur, poisoning of the catalyst and consequent loss of activity proceed rapidly and the life of the catalyst becomes impractically short.

SUMMARY OF THE INVENTION

It has now been found that the promoted copper catalyst in question, that catalyst consisting essentially of a mixture of finely divided copper metal and a minor proportion of at least one activator metal of the group consisting of silver, platinum, palladium, manganese, cobalt, nickel, chromium, and molybdenum supported on gamma-alumina having a surface area of at least about 10 sq meters per gram, is substantially enhanced in both catalytic activity and in resistance to poisoning by sulfur compounds by impregnating the active catalyst with about 0.01–0.3 gram mole of alkali metal hydroxide per 100 grams of catalyst and roasting the impregnated catalyst at a temperature up to about 650° C sufficient to cause a reaction of the alkali metal hydroxide with the alumina surface. The so-treated catalyst is activated for use by contacting it with hydrogen at about 100° C–400° C for a time sufficient to convert essentially all copper and activator metal present to the metallic state.

DETAILED DESCRIPTION OF THE INVENTION

This alkali treatment is similarly effective for both unused active catalyst and catalyst which has been reactivated after poisoning by sulfur compounds. In the latter case, the poisoning sulfur compounds or their reaction products are first removed from the catalyst by a procedure disclosed in U.S. Pat. No. 3,327,013. This process of reactivation comprises the steps of (1) roasting the poisoned catalyst in an oxygen-containing atmosphere at about 400° C–700° C, (2) impregnating the roasted catalyst with alkali metal hydroxide solution, (3) heating the impregnated catalyst at about 350° C–650° C, and then (4) leaching the heated impregnated catalyst with water to remove the thereby oxidized and solubilized sulfur compounds. The leached and dried catalyst is then reimpregnated with about 0.01–0.3 gram mole of alkali metal hydroxide per 100 grams of catalyst as previously specified to enhance its restored activity. Roasting of the alkali-impregnated active catalyst can be carried out at about 350° C–650° C, preferably at about 400° C–500° C.

As set forth above, the catalyst consists essentially of a mixture of finely divided copper metal and a minor proportion of at least one activator metal supported on gamma-alumina having a surface area of at least 10 sq meters per gram. Preferably, the copper metal comprises about 3 to 13 percent by weight of the alumina.

The metals useful as activators in the catalyst of this invention are metals which are normally, or can be, polyvalent and whose oxides are reducible by hydrogen or a hydrogen-inert gas mixture at a temperature below about 350° C–400° C. Preferably, the weight of activator metal or metals is less than the weight of copper in the catalyst and most preferably is about 1 to 20 percent of the combined weight of copper and activator. Suitable activator metals include silver, platinum, palladium, manganese, nickel, cobalt, chromium, and molybdenum.

The support employed is a gamma-alumina having a high surface area (BET surface area) of at least 10 sq meters per gram and preferably with particle sizes in the range of those substantially passing a No. 8 sieve (U.S. Sieve Series) to those passing a No. 18 sieve, but generally retained on a No. 30 sieve. A finer grade of gamma-alumina may be employed if the gamma-alumina is first granulated to provide particle sizes in the specified range. It is also preferable but not essential when the catalyst is subjected to the present alkali treatment prior to use that the gamma-alumina contain about 0.1 to 1.5 percent by weight of sodium, present in combined form with the alumina and reported as $Na_2O$.

In carrying out the preparation of the present catalyst, a relatively concentrated aqueous solution containing copper is preferably prepared by dissolving about 2.5 to 3 parts by weight of a water-soluble copper salt in 1 part by weight of water. More preferably, the water is acidified with about 5 to 10 percent by weight of nitric acid. Cupric nitrate is the preferred copper salt because of its solubility and also because residual small amounts of halide, sulfate, or other sulfur-containing ions may persist and adversely affect the activity of the final copper hydrogenation catalyst. Less soluble salts such as the acetate and formate can also be used. Similar water-soluble salts of any activator metals to be employed are dissolved in the copper salt solution in the requisite amount. This aqueous solution is poured onto a quantity of gamma-alumina in the amount required to provide from about 3 to about 13 percent by weight of reduced metal based on the total weight of the prepared agent. The mixture is stirred briefly and then dried, as in a 110° C oven, and then roasted at a temperature of about 250° C–400° C, and more preferably 290° C–400° C. During roasting, the copper salts and activator metal salts are converted to oxides or anhydrous metal salts in such a manner that a single phase is formed with these metal compounds and the alumina, as determined on examination by X-ray diffraction. This step is not completely understood but is essential to the proper preparation of the present highly efficient, high capacity catalyst.

Preparation of the catalyst in reduced metal form is completed upon passing a stream of hydrogen, more preferably a mixture of hydrogen and an inert gas such as nitrogen, argon, or helium, over a bed of the roasted material for about 30 minutes or more while the bed is maintained at a temperature of about 100° C–400° C, thus reducing the roasted material to metal form. About two times the stoichiometric amount of hydrogen suffices to make the reduction as complete as desired. The resulting product consists of extremely finely divided "black" copper, with admixed activator metal, intimately and widely dispersed throughout a high surface area gamma-alumina.

While earlier known catalysts when freshly prepared exhibit a higher efficiency after having been reoxidized once and again reduced, the present catalyst does not need such special treatment, though such treatment does not adversely affect its performance.

However, the reduction temperature critically affects its catalytic efficiency. If reduction temperatures are unduly high, sintering of the metal crystallites tends to occur with resulting lowering in efficiency and capacity. Generally, a reduction temperature of about 250° C–300° C is preferred, and especially a temperature of about 270° C.

Alkali impregnation of unused catalyst to enhance its activity and raise its resistance to poisoning by sulfur can be done either immediately before or after the reduction with hydrogen.

Sodium hydroxide is the preferred alkali used in both the alkali impregnation of active catalyst and the alkali treatment of roasted sulfur-poisoned catalyst to remove sulfur compounds. Other alkali metal hydroxides can be used in the same way to obtain similar results. These alkalis include potassium hydroxide, lithium hydroxide, and cesium hydroxide. The concentration of alkali solution depends upon the quantity of alkali to be deposited on the catalyst, since it is preferable to use that volume of solution which will just saturate the quantity of catalyst being impregnated in order to produce a uniform product. In practice, aqueous sodium hydroxide of about 3 to 13 percent concentration will provide catalyst containing a preferred 0.02–0.1 gram mole of NaOH per 100 grams. Of course, solutions of alkali in other inert volatile solvents such as methanol or ethanol can be used as well.

PREPARATION OF CATALYST

The following promoted copper catalysts were prepared and are representative of those to which the alkali impregnation process of the present invention is applicable.

A. A portion of gamma-alumina containing 0.1 to 1.5 percent by weight $Na_2O$ and having particle sizes substantially all passing a No. 8 to a No. 18 sieve (U.S. Sieve Series) was impregnated with an aqueous solution of cupric and nickel nitrates containing 99 parts of copper per part of nickel. The impregnated gamma-alumina was dried and roasted, thus converting the metal salts to a light-green mixed oxide of copper and aluminum present as a single phase. The roasted material was then treated with a mixture of nitrogen and hydrogen at a temperature of 250° C for a sufficient period (about 3 hours) for the oxides to be reduced to the metal. The total metal content of the resulting supported catalyst was about 5 percent by weight.

B. 38.5 Grams of activated alumina containing 0.1 to 1.5 percent by weight $Na_2O$ and having particle sizes substantially all passing a No. 8 to a No. 18 sieve were impregnated with 14 milliliters of an aqueous solution containing 8.7 grams of $Cu(NO_2)_2.3H_2O$ and 0.89 gram of $AgNO_3$. The impregnated alumina was dried for one hour at 100° C, then roasted at 350° C for 3 hours to form a light-green mixed oxide of copper, silver and aluminum present as a single phase, and finally, the oxide was reduced at 290° C with a nitrogen-hydrogen mixture to yield alumina impregnated with black, finely-divided metal. The metal consisted of 90 percent of copper and 10 percent of silver. The metal content of the catalyst prepared was about 6.5 weight percent.

C. A portion of activated gamma-alumina containing 0.1 to 1.5 percent by weight $Na_2O$ and having particle sizes substantially all passing a No. 8 to a No. 18 sieve was impregnated with an aqueous solution of cupric nitrate and silver nitrate containing 4 parts of copper per part of silver. The impregnated alumina was dried for one hour at 110° C, then roasted at 350° C for 3 hours to form a light-green mixed oxide of copper, silver and aluminum present as a single phase, and finally, this oxide was reduced at 290° C with a nitrogen-hydrogen mixture to yield alumina impregnated with black, finely-divided metal. The metal consisted of 80 percent by weight of copper and 20 percent by weight of silver. The metal content of the catalyst was 6.8 weight percent.

D. A 41.5-gram portion of an activated gamma-alumina having a surface area greater than 10 sq meters per gram containing 0.1 to 1.5 percent by weight $Na_2O$ and having particle sizes substantially all passing a No. 8 to a No. 18 sieve was impregnated with 12 milliliters of an aqueous solution containing 6.8 grams of $Cu(NO_3)_2.3H_2O$ and 5.45 grams of $Ni(NO_3)_2.6H_2O$. The impregnated alumina was dried for 2 hours at 110° C and then roasted at 350° C for 3 hours to form a light-green mixed oxide of copper, nickel and aluminum present as a single phase. Reduction of the copper and nickel oxides to the respective metals was effected with hydrogen at 400° C. The reduced metal consisted of 3 parts of copper per 2 parts by weight of nickel. The metal content of the catalyst was about 6.6 weight percent.

E. 10 Grams of $Ni(NO_3)_2.6H_2O$, 4 grams of $Co(NO_3)_2.6H_2O$, 4 grams of $Cr(NO_3)_3.9H_2O$, 8 grams of 50 percent by weight $Mn(NO_3)_2$ aqueous solution and 1.0 gram of $AgNO_3$ were dissolved in an aqueous solution consisting of 100 milliliters of water plus 10 milliliters of concentrated nitric acid (16 normal). After solution of the above salts was complete, 280 grams of $Cu(NO_2)_2.3H_2O$ were dissolved in solution yielding a total of 240 milliliters of impregnating solution. This impregnating solution was dispersed on 747 grams of gamma-alumina. The gamma-alumina contained 1.18 percent by weight of $Na_2O$. In addition, the gamma-alumina had a surface area of about 177 sq meters per gram and a particle size such that the gamma-alumina passed a No. 8 sieve and was retained on a No. 18 sieve. The impregnated alumina was dried at about 160° C for about 2 hours. The dried material was then roasted at 400° C for about 5 hours. At this time, the impregnated alumina was an olive-green color. On X-ray diffraction examination, no separate phase for copper oxide was detected. Instead, all the metal oxides had been transformed into a single phase. The copper oxide and activator metal oxides were reduced at about 300° C by passing a stream of 90 percent by volume nitrogen and 10 percent hydrogen through a column packed with the impregnated and roasted alumina. Reduction of the metal oxides to metallic form was completed in about 30 minutes.

EXAMPLE 1

A 1400-g portion of copper plus activator metals on $Al_2O_3$ catalyst prepared as described in (E.) above was uniformly wet with 406 g of 5 percent NaOH solution in a rotating jar mixer. The alkali-impregnated catalyst was partially dried in the mixer using a hot air blower at 300° C for 15 minutes, then the catalyst was roasted for 6 hours in an oven set at 440° C. The roasted catalyst showed a weight gain corresponding to about 1.15 percent $Na_2O$ or 0.037 gram mole as NaOH per 100 grams of anhydrous roasted catalyst. A number of batches of alkalized catalyst were prepared by this procedure. It was found that uniformly good results were obtained by a standardized procedure consisting of these steps:

(1) Impregnate catalyst with aqueous NaOH essentially as shown.
(2) Dry partially at 125° C–150° C to remove at least half of the water.
(3) Roast at 400° C for 2 hours.
(4) Cool to 50° C and remove fine dust (less than 0.1 percent loss).

The alkali-impregnated and roasted catalyst batches were combined in a tubular steel reactor and the catalyst was reduced at 310° C for 16 hours with 71l/min of 98.6 percent $N_2$-1.4 percent $H_2$ mixture passing through a 20-kg bed of catalyst. After the reduction, the catalyst bed was pressurized to 60 psig with nitrogen and allowed to cool to about ambient temperature.

The catalyst bed was then used to hydrogenate alpha-acetylenes selectively in a liquid $C_4$ fraction according to the process of U.S. Pat. No. 3,912,789. The $C_4$ fraction contained 0.5 percent alpha-acetylenes and about 50 percent 1,3-butadiene with the remainder largely butenes and butanes. The fraction contained about 2 ppm by weight of sulfur. The liquid $C_4$ feed to the reactor was first pressurized with hydrogen at about 300 psig so as to contain dissolved hydrogen and then was passed at an average space velocity of 4–5 liquid vol/-vol/hr through the catalyst bed using a mixture of 2 parts of fresh feed with 3 parts of recycled hydrocarbon product. The process was run for a total of 25 days under these conditions, starting with a catalyst bed temperature of 36° C and an effluent hydrocarbon product containing 30 parts per million of alpha-acetylenes. The catalyst temperature was raised progressively as necessary during the 25-day run to keep the acetylene content of the effluent product at or below that value. On the twenty-fifth day, the bed temperature was raised from 54° C to 55° C, thereby reducing the effluent acetylene content from 22 ppm to 7 ppm. The experiment was ended at this point.

Under process conditions otherwise the same, the activated copper catalyst with no alkali treatment had to be run at half the above liquid space velocity to produce hydrocarbon effluent with the same maximum acetylene content.

EXAMPLE 2

A Cu plus activator metals on gamma-$Al_2O_3$ catalyst similar to that of Example 1 had lost much of its activity as a hydrogenation catalyst after exposure over about 9 weeks' total process time to liquid $C_4$ streams containing $H_2S$ and lower alkyl mercaptans and sulfides at the 2–50 ppm level had caused an accumulation of about 0.5 percent by weight of sulfur in the catalyst. This poisoned catalyst was roasted in air at about 400° C–450° C for 24 hours. Portions of 1400 g of roasted catalyst were each uniformly wet with 397 g of 6.8 percent aqueous NaOH and partially dried at about 150° C, then roasted in air at 450° C for 2 hours. Four such portions of roasted catalyst were combined in a 24.5 cm diameter column and washed at 25° C by a stream of deionized water introduced into the bottom of the column and overflowing at the top until the overflow was essentially free of dissolved solids. This required about 150 liters of wash water. The washed catalyst was then dried at 300° C. When reduced by hydrogen at this point, the regenerated catalyst shows moderate activity comparable to that of the non-alkalized catalyst described in Example 1. However, this catalyst was reimpregnated with aqueous NaOH, roasted at about 450° C, and reduced with a nitrogen-hydrogen mixture as described in Example 1. This regenerated and re-alkalized catalyst containing about 1.5 percent NaOH then had superior hydrogenation activity similar to its activity prior to being poisoned.

Similar enhancement of catalytic activity and resistance to poisoning by sulfur compounds is found when the catalysts of sections A, B, C, and D above are impregnated with NaOH or other alkali metal hydroxide as set forth previously. These alkalized catalysts and other catalysts of the invention are also restored to essentially their original high activity after activity has been impaired by excessive exposure to sulfur compounds when they are subjected to the alkali treatment, water wash, and reimpregnation with alkali process described in Example 2.

We claim:
1. A process for improving an active catalyst consisting essentially of a mixture of finely divided copper metal and a minor proportion of at least one activator metal of the group consisting of silver, platinum, palladium, manganese, cobalt, nickel, chromium, and molybdenum supported on gamma-alumina having a surface area of at least about 10 sq meters per gram, which process consists essentially of impregnating said catalyst with about 0.01–0.3 gram mole of alkali metal hydroxide solution per 100 grams of catalyst, roasting the impregnated catalyst at a temperature up to about 650° C sufficient to cause a reaction between the alkali metal hydroxide and the alumina surface, and contacting the roasted alkali-impregnated catalyst with hydrogen at about 100° C–400° C for a time sufficient to convert essentially all copper and activator metal present to the metallic state.

2. The process of claim 1 wherein the roasted alkali-impregnated catalyst is contacted at about 250° C–300° C with a mixture of hydrogen and an inert gas.

3. The process of claim 1 wherein the alkali metal hydroxide is sodium hydroxide.

4. The process of claim 1 wherein an aqueous solution of alkali metal hydroxide is used to impregnate the catalyst.

5. The process of claim 1 wherein the catalyst contains about 3–13 percent of copper based on the weight of alumina and the activator metal content is about 1–20 percent of the combined weight of copper and activator metal, said catalyst is impregnated with about 0.01–0.3 gram mole of aqueous solution of sodium hydroxide per 100 grams of catalyst, the impregnated catalyst is roasted at about 400° C–500° C, and the roasted catalyst is contacted at about 250° C–300° C with a mixture of hydrogen and an inert gas for a time sufficient to convert essentially all copper and activator metal present to the metallic state.

6. The process of claim 5 wherein the activator metal is a mixture of silver, chromium, nickel, cobalt, and manganese.

* * * * *